United States Patent
Rathbone et al.

(10) Patent No.: US 6,663,608 B2
(45) Date of Patent: *Dec. 16, 2003

(54) SYNCHRONIZING OF ANIMAL OESTRUS AND INTRA VAGINAL DEVICES USEFUL THEREIN

(75) Inventors: Michael John Rathbone, Hamilton (NZ); Craig Robert Bunt, Hamilton (NZ); Shane Burggaaf, Hamilton (NZ)

(73) Assignee: Interag, Hamilton (NZ)

(*) Notice: Subject to any disclaimer, the term of this patent is extended or adjusted under 35 U.S.C. 154(b) by 150 days.

This patent is subject to a terminal disclaimer.

(21) Appl. No.: 09/973,901

(22) Filed: Oct. 11, 2001

(65) Prior Publication Data

US 2002/0058926 A1 May 16, 2002

Related U.S. Application Data

(63) Continuation of application No. 09/180,076, filed as application No. PCT/NZ97/00052 on Apr. 30, 1997.

(30) Foreign Application Priority Data

May 1, 1996 (NZ) .............................................. 286492

(51) Int. Cl.[7] .............................................. A61M 31/00
(52) U.S. Cl. ...................................... 604/286; 604/515
(58) Field of Search .......................... 604/890.1, 891.1, 604/19, 522, 57, 327–331, 364, 368, 374, 385.17, 285–288, 500, 515; 424/486; 528/15

(56) References Cited

U.S. PATENT DOCUMENTS

| 3,545,439 A | 12/1970 | Duncan |
| 3,920,805 A | 11/1975 | Roseman |
| 4,012,496 A | 3/1977 | Schopflin et al. |
| 4,014,987 A | 3/1977 | Heller et al. |
| 4,016,251 A | 4/1977 | Higuchi et al. |
| 4,402,695 A | 9/1983 | Wong |
| 4,961,931 A | 10/1990 | Wong |
| 5,398,698 A | 3/1995 | Hiller et al. |
| 5,597,584 A * | 1/1997 | Bhatt et al. ................. 424/486 |
| 6,423,039 B1 * | 7/2002 | Rathbone et al. ........... 604/286 |

FOREIGN PATENT DOCUMENTS

AU    70919/81    12/1981

OTHER PUBLICATIONS

Drug Development and Industrial Pharmacy, 11(6&7), 1271–1312 (1985) "Intravaginal Controlled Administration of Flurogestone Acetate: (III) Development of Rate–control Vaginal Devices", Mohan Kabadi and Yie W. Chien, Copyright 1985 by Marcel Dekker, Inc.

"In Vitro and In Vivo Considerations of a Novel Matrix–Controlled Bovine Progesterone–Releasing Intravaginal Device", V. W. Winkler, S. Borodkin, S.K. Webel and J.T. Mannebach, pp. 816–818, Journal of Pharmaceutical Sciences.

"Intravaginal Controlled Administration of Flurogestone Acetate II: Development of an In Vitro System for Studying the Intravaginal Release and Permeation of Flurogestone Acetate", Mohan B. Kabadi and Yie W. Chien, pp. 1464–1468, Journal of Pharmaceutical Sciences vol. 73, No. 10, Oct. 1984,, © 1984, American Pharmaceutical Association.

(List continued on next page.)

Primary Examiner—Brian L. Casler
Assistant Examiner—Michael M Thompson
(74) Attorney, Agent, or Firm—Jacobson Holman PLLC

(57) ABSTRACT

An intra vaginal device which is of a variable geometry and which includes a silicone matrix impregnated with progesterone, the confirmation and content of the progesterone impregnated matrix being such as to optimise effectiveness with a lower initial loading of progesterone.

7 Claims, 16 Drawing Sheets

OTHER PUBLICATIONS

"Intravaginal Controlled Administration of Flurogestone Acetate I: Development of a Stability–Indicating Liquid Chromatographic Method and Stability Kinetics of Flurogestone Acetate", Mohan B. Kabadi, Kirti H. Valia and Yie W. Chien, ©1984, American Pharmaceutical Association, pp. 1461–1464, Journal of Pharmaceutical Sciences, vol. 73, No. 10, Oct. 1984.

Intravaginal Controlled Administration of Flurogestone Acetate: (IV) In Vitro—In Vivo Correlation for Intravaginal Drug Delivery From Rate—Control Vaginal Pessary, Drug Development and Industrial Pharmacy 11 (6&7), 1313–1361 (1985)—Kabadi and Chien.

Journal of Reproduction & Fertility, No. 46, Roche, "Retention rate in cows and heifers . . . ", 1976, pp. 253–255.

Department of Animal Science, Kinder et al, "Progestin and Estrogen Regulation of Pulsatile . . . ", Feb. 2, 1996, pp. 1424–1440.

Biology of Reproduction, No. 26, Kesner et al, "Estradiol Induces and Progesterone . . . ", 1982, pp. 571–578.

Article—Published by the Controlled Release Society, Inc., Proceedings of the 24th International Symposium on Controlled Release of Bioactive Materials, Jun. 15–19, 1997, Stockholm, Sweden, ISSN 1022–1078.

* cited by examiner

FIG. 1'A
FIG. 1'B
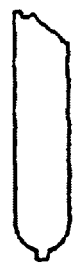
FIG. 1'C
FIG. 1'D
FIG. 1'E
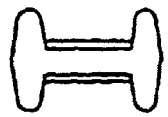

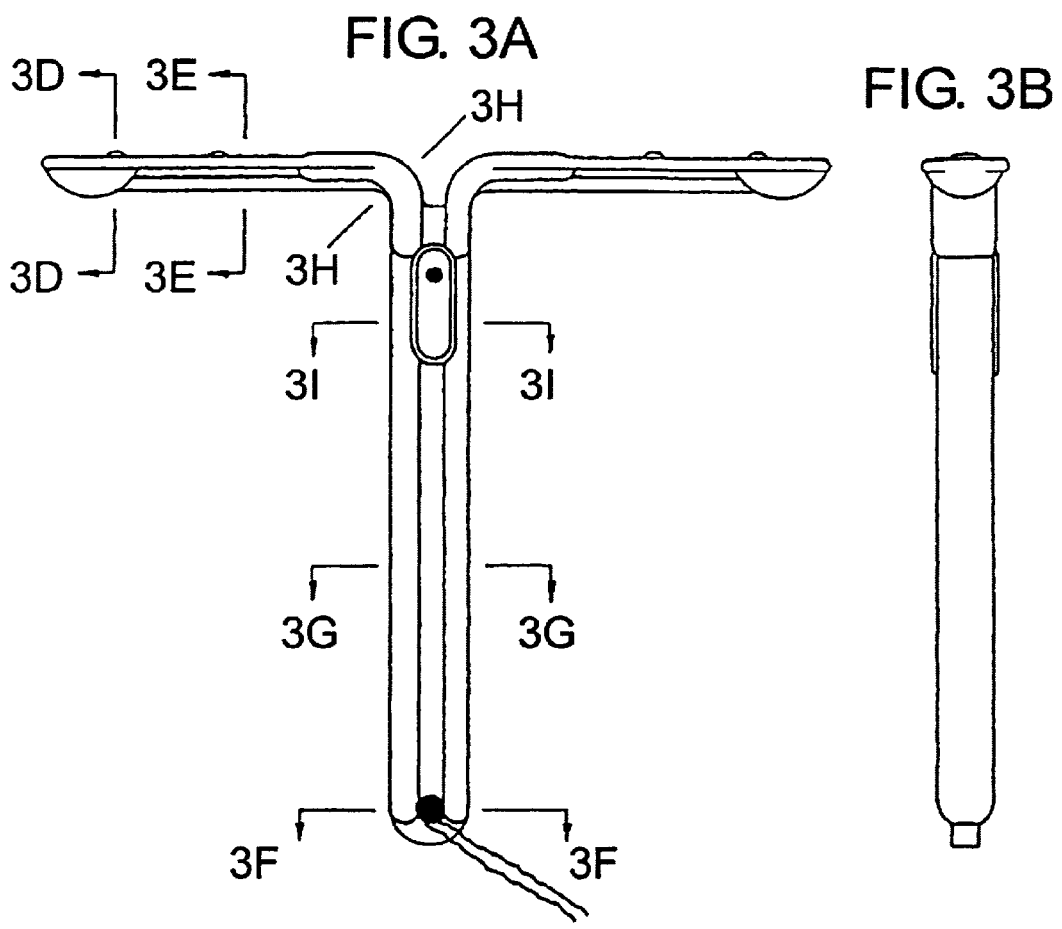
FIG. 3A  FIG. 3B
FIG. 3C
FIG. 3E  FIG. 3D  FIG. 3F  FIG. 3G  FIG. 3H
  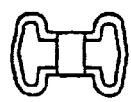  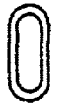
FIG. 3I

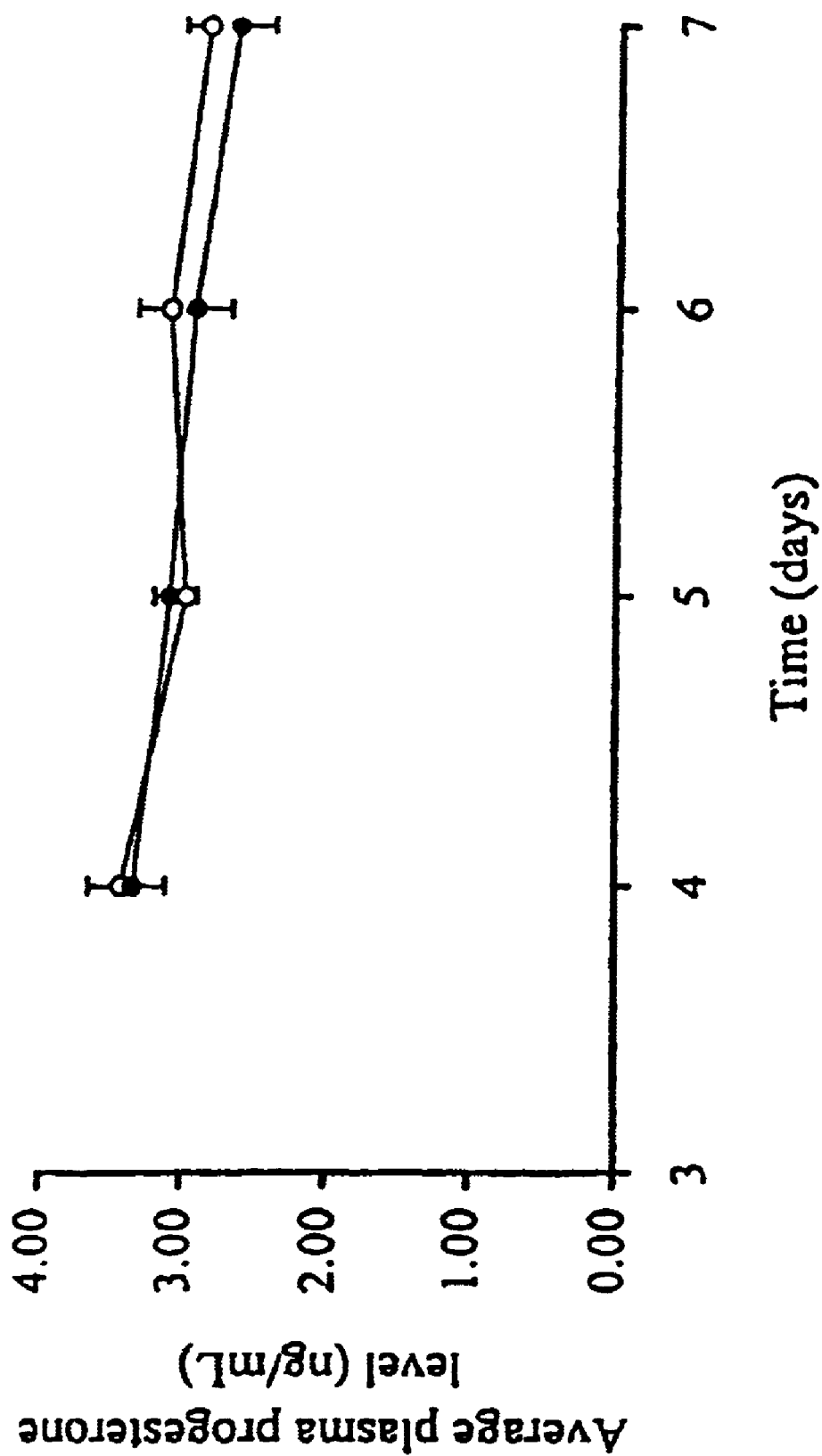

SYNCHRONIZING OF ANIMAL OESTRUS AND INTRA VAGINAL DEVICES USEFUL THEREIN

This is a Continuation of application Ser. No. 09/180,076 filed Oct. 30, 1998. which in turn is a U.S. national phase of PCT/NZ97/00052 filed Apr. 30, 1997.

TECHNICAL FIELD

The present invention relates to improvements in and/or relating to the synchronising of animal oestrus and intra vaginal devices useful therein together with related means and methods.

BACKGROUND ART

It is useful for farmers to synchronise the oestrus of animals whether they be cattle beasts (whether for dairy or beef purposes) sheep, goats, horses, or the like where artificial insemination is practised. By way of example, in relation to cattle beasts, in a normal 365 day year 282 days on average is taken up of the year with the gestation period itself. With approximately 30 days to recover after delivery of its progeny each cow therefore has an average of only two and a half cycles if there is to be a timely management of the herd. Thus it is important over that remaining period of less than 53 days to ensure each cow in a herd becomes pregnant.

The traditional method of mating dairy cows with bulls is now largely superseded by the use of artificial insemination procedures which offer the prospect of rapid herd improvements although bulls are still presented to the herd frequently to catch those animals that have not conceived by the artificial insemination procedure.

There is therefore a great advantage attached to bringing such herd animals into oestrus simultaneously so as to make it easier to ensure effective usage of the artificial insemination procedure and subsequently to enable still within the "window" a further prospect of artificial insemination of those animals synchronistically brought to oestrus that have not already conceived.

Various means of achieving such a management of the synchronisation of the coming into oestrus of cows (whether heifers or lactating cows) and even sheep and goats has been disclosed in the art which includes the "EAZI-BREED CIDR Controlled Breeding and Reproductive Management" booklet made available to interested parties by InterAg a division of the applicant company in respect of its intra vaginal Eazi-Breed™ CIDR® product line.

The disclosures in the aforementioned publication, the full contents of which are here included by way of reference, comprehensively describe treatment protocols applicable at least to New Zealand herds of cattle beasts for synchronising oestrus and treatment of anoestrus.

These treatment protocols often utilise Eazi-Breed™ CIDR® devices in combination with drugs such as prostaglandin and/or oestradiol benzoate, and extend in general for periods of 7, 10 or 12 days.

If both control of the oestrus cycle and high fertility are to be optimised in cattle, studies have shown that an intra vaginal device must deliver sufficient progesterone (when used with combination drugs i.e. oestradiol or GnRH) to produce a minimum plasma progesterone concentration of 2 ng/mL over the terminal period of treatment (1, 2).
1. Kesner, J. S., Padmanabhan, V. and Convey, E. M. Biol. Reprod. 26 (1982) 571–578.
2. Kinder, J. E., Kojima, F. N., Bergfeld, E. G. M., Wehrman, M. E. and Fike, K. E. J. Anim. Sci 74 (1996) 1424–1440.

A cost factor arises in the adoption of such protocols as a farmer is faced with the costs of the intra vaginal progesterone containing device as well as the use of the combination drugs. This ignores also the economic cost of the artificial breeding materials themselves.

The intra vaginal progesterone containing devices hitherto used in New Zealand and to a large extent elsewhere are typified by the CIDR® product of the applicant company depicted hereinafter in FIG. 1 being a variable geometry device for vaginal insertion and retention which comprises a structural frame of a metal or appropriate plastics material encased in a progesterone impregnated plastics material from which the material can leach in the vaginal environment and from which it can be timely withdrawn by appropriate means (e.g: a string, tail or a tool) to allow the animal to progress into oestrus shortly after the removal. Hereinafter the aforementioned device will be referred to by its registered trademark CIDR®.

Another product available in the market place of this kind is another variable geometry device and such a device is depicted hereinafter in FIG. 2. Such a device is a helical coil capable of being helically tightened and which is retainable in its helical form in the animals vagina. The device includes a withdrawal cord and carries a gelatine capsule which includes oestradiol benzoate so that there can be co-administration of the progesterone to be released over a protracted period and the oestradiol benzoate which is to be released at a different rate. Such a device includes a progesterone impregnated plastics matrix about a helical spine. Such a device is available from Sanofi Animal Health Limited, PO Box 209, Rhodes Way, Watford, Herts, WD24QE, England under its registered trademark PRID®.

The aforementioned CIDR® and PRID® devices are manufactured in large volumes with the most expensive material being the progesterone active ingredient and thus small reductions in the progesterone inclusion in such devices will provide an economic advantage to a producer and to a farmer. Also any such reduction provides a reduced risk to the environment owing to a likely reduced residual amount of the progesterone in the matrix after the device has been withdrawn from an animal. This reduced residual amount not only provides safety but also dis-encourages the unrecommended reuse of a device in another animal where the unknown condition of such a device will give unpredictable results.

The CIDR® prior art device of the applicant company has been marketed with a silicone plastics matrix about its spine which contains about 1.9 grams of progesterone (USP) which drops to 1.33 grams still retained in the silicone matrix if the device is withdrawn after seven days. The same device drops to 1.05 grams of progesterone if it is not withdrawn until after 12 days.

The PRID® coil intra vaginal device contains at the outset 1.55 grams of progesterone which reduces down to 1.18 grams after 7 days and down to 0.94 grams after 10 days. The leach rate from the PRID® product may be affected in part by the inclusion of inorganic materials in the silicone plastics material such as calcium carbonate. The CIDR® silicone matrix is largely free of any such inclusions.

Hoechst U.S. Pat. No. 5,398,698 discloses the use of milled sheets of silicone rubber in intra-vaginal devices which carry progesterone. The milled sheets (2 to 10 mm thick) are vulcanised for from 4 to 8 minutes at from 70° C. to 120° C.

The accepted test for the delivery of progesterone or its metabolites to the appropriate site of action in order to postpone oestrus is by reference to the progesterone level in the blood plasma of the animal. The design of such devices has to date usually been on the basis of an acceptance of the Higuchi equation based on a square root of time model (see hereinafter) which suggests that progesterone inclusions in such a plastics matrix would achieve plasma levels which decline with time.

Our investigations have found surprisingly that it is inappropriate in the design of such intra vaginal devices to rely upon the Higuchi equation or the square root of time model. In our device release is constant with time up to 7 days resulting in constant steady state plasma levels over that time period.

We have determined that by modifying the levels of progesterone initially in a silicone matrix, by controlling the thickness of the silicone matrix over the spine and by giving attention to the surface area of the device savings to a manufacturer arising from reduced quantities of progesterone being needed while at the same time achieving the same blood levels can be achieved. Savings are also achieved over the prior art devices in terms of the amount of silicone used, since silicone is the second-most costly material used in the devices, with corresponding benefits being able to be passed on to the user.

The present invention relates to intra vaginal devices, methods of producing intra vaginal devices, and the use of such intra vaginal devices for managing oestrus and for the treatment of anoestrus in cattle, sheep, deer and goats.

DISCLOSURE OF INVENTION

In one aspect the invention is an intra vaginal device of a variable geometry kind capable of being applied into the vaginal cavity of an animal selected from the group consisting of cattle, sheep, deer and goats, retainable therein over a period of time within the range of from 7 to 12 days and then to be withdrawable therefrom to allow the onset of oestrus, said device being characterised in that:

a matrix of a cured silicone rubber material that includes greater than 5% by weight progesterone to the weight of the matrix defines an exterior surface (which may be all or part only of the device) of at least 75 cm$^2$ contactable once inserted in the vagina of such an animal by the vaginal membrane and/or vaginal fluid(s) of the animal, the matrix of progesterone containing silicone rubber material has been formed by injection of the uncured progesterone containing matrix as a liquid into a mould for a sufficient time to achieve at a mould temperature or temperatures within the range of from 100° C. to 210° C. and a shape retaining at least partial cure thereof, the total progesterone load (irrespective of whether alpha or beta progesterone or mixtures thereof) being from 1 to 1.5 grams within said matrix, said surface area is available to at least substantially all of the matrix for progesterone release over a thickness of no greater than about 1 millimeter, and said device upon vaginal insertion into such an animal is able to achieve and then maintain in the animal for a least seven days a minimum progesterone blood plasma level of 2 nanograms per milliliter of plasma of the animal and which after seven days of insertion will have a residual load in the silicone rubber matrix of less than 65% by weight of its progesterone load at insertion.

Preferably said exterior surface is from 100 to 150 cm$^2$, more preferably 120 to 125 cm$^2$.

Preferably said matrix has about 10% by weight progesterone by weight of progesterone to the weight of matrix.

Preferably said matrix at least in part encases a deformable frame.

Preferably said frame is resilient.

Preferably said frame is substantially in the form of a "T" with the arms of the "T" being deformable to allow introduction into the vagina of an animal, the "T" form being defined by a resilient spine about which (at least in part) there is moulded said matrix.

Preferably said frame is of nylon.

Preferably after seven days, from insertion the matrix will have a residual load of less than 60% by weight of its progesterone load at insertion.

In a further aspect the invention is an intra vaginal device of a variable geometry kind capable of being applied into the vaginal cavity of an animal selected from the group consisting of cattle, sheep, deer and goats, retainable therein over a period of time within the range of from 7 to 12 days and then to be withdrawable therefrom to allow the onset of oestrus, said device being characterised in that on a frame or spine (hereafter "frame") of variable geometry there is a matrix of a cured silicone rubber material that includes greater than 5% and less than 20% by weight progesterone to the weight of the matrix defines and exterior surface (which may be all or part only of the device) of at least 100 cm$^2$ contactable once inserted in the vagina of such an animal by the vaginal membrane and/or vaginal fluid(s) of the animal, the matrix of progesterone containing silicone rubber material has been formed by injection of the uncured progesterone containing matrix as a liquid into a mould for a sufficient time to achieve at a mould temperature of temperatures within the range of from 190° C. to 195° C. and a shape retaining at least partial cure thereof, the total progesterone load (irrespective of whether alpha or beta progesterone or mixtures thereof) being from 1 to 1.5 grams preferably about 1.35 grams) within said matrix, said surface area is available to at least substantially all of the matrix for progesterone release over a thickness of no greater than about 1 millimeter, and said device upon vaginal insertion into such an animal is able to achieve and then maintain in the animal for at least seven days a minimum progesterone blood plasma level of 2 nanograms per milliliter of plasma of the animal and which after seven days from insertion will have a residual load in the silicone rubber matrix of less than 65% by weight of its progesterone load at insertion.

Preferably said device is substantially as herein defined with reference to any one or more of the accompanying drawings.

In still a further aspect the invention a method of postponing oestrus or treatment of anoestrus in an animal which includes the steps of administering into said animal by means of an intra vaginal device sufficient progesterone from a progesterone impregnated silicone rubber matrix where the progesterone content in the matrix is 5% or greater by weight via a surface area greater than 75 cm$^2$ so as to achieve on the last few days of insertion a progesterone blood plasma level of greater than 2 nanograms per milliliter, and removing the device after an insertion period of from 7 to 12 days.

Preferably said device is as previously defined.

Preferably said method includes the administration of oestradiol at or near the time of insertion of said device.

Preferably said method includes the administration of a prostaglandin at about day 6 of about a 7 to 10 day device insertion period.

In still a further aspect the invention is, in a method of attempting to synchronise the onset of oestrus of a herd of cattle beasts, the procedure of administering intra vaginally to each animal of the herd progesterone from an intra vaginal device of the present invention and after an appropriate period of time removing such devices to allow the onset of oestrus (the procedure optionally including the steps of administration of oestradiol benzoate and/or prostaglandin etc. as known in the art or otherwise), said method being further characterised in that levels of progesterone in the blood plasma of each animal is greater than 2 nanograms per milliliter until such time as the devices are withdrawn, In still a further aspect the invention consists in a method of synchronising the onset of oestrus in a herd of cattle beasts which comprises administering by means of an intra vaginal device to each animal from a progesterone impregnated matrix of the device an effective amount of progesterone for the period the device is retained intra vaginally, the device having being administered with a progesterone quantity of about 1.35 grams and being removed with a progesterone quantity of the order of about 0.85 grams.

As used here in "surface area" of the progesterone impregnated matrix is that area directly contactable by vaginal fluid(s) and/or membrane.

As used herein "surface area" is independent of any surface area of the spine (if any) which may or may not be of a plastics material. However, thicknesses of the progesterone impregnated medium or matrix are to the surface of the spine.

While reference has been made to cattle beasts the device and method is believed to be equally applicable to other mammals, e.g. sheep, goat, horse, etc.

BRIEF DESCRIPTION OF DRAWINGS

The present invention will now be described with reference to the accompanying drawings in which:

FIG. 1 shows a series of drawings (a) through (e) of a prior art EaziBreed™ CIDR™ product of this company having a progesterone impregnated silicone matrix of an average depth of about 1.5 mm but having the depth thereof varying greatly.

FIG. 1' shows the preferred spine of the prior art device, a spine which with no or little modification is useful in a device in accordance with the present invention, FIG. 1'A shows an elevation of the spine, FIG. 1'B showing a side elevation of the spine, FIG. 1'C showing the plan view of the top arms of the device, FIG. 1'D shows the section at "AA", FIG. 1'E shows the section at "BB", FIG. 3A shows an elevation of the (CIDR-B™) device in accordance with the present invention, FIG. 3B shows the side elevation of the device of FIG. 3A, FIG. 3C shows a plan view of the top of the device as shown in FIGS. 3A and 3B, FIG. 3D shows a section at "DD" of FIG. 3A, FIG. 3E shows a section at "CC"" of FIG. 3A, FIG. 3F shows a section at "BB" of FIG. 3A, FIG. 3G shows a section at "AA' of FIG. 3A, FIG. 3H shows a section at "PP" of FIG. 3A, being the hinging region of the arms from the body, and FIG. 3I is the section "HH" of FIG. 3A, and FIGS. 4 through 15 show results, plots, models and concepts hereinafter described in greater detail.

DETAILED DESCRIPTION

The device of the present invention will now be described with reference to both in vitro and in vivo studies. In the following description the reference to the CIDR™, device is by reference to the device of the form depicted in FIGS. 1A to 1E. The reference hereafter to the device of the present invention (to be known as the CIDR-B™ device) is preferably that substantially as depicted in FIGS. 3A through 3I and described hereinafter in more detail.

In vitro Studies

Figure 1A:
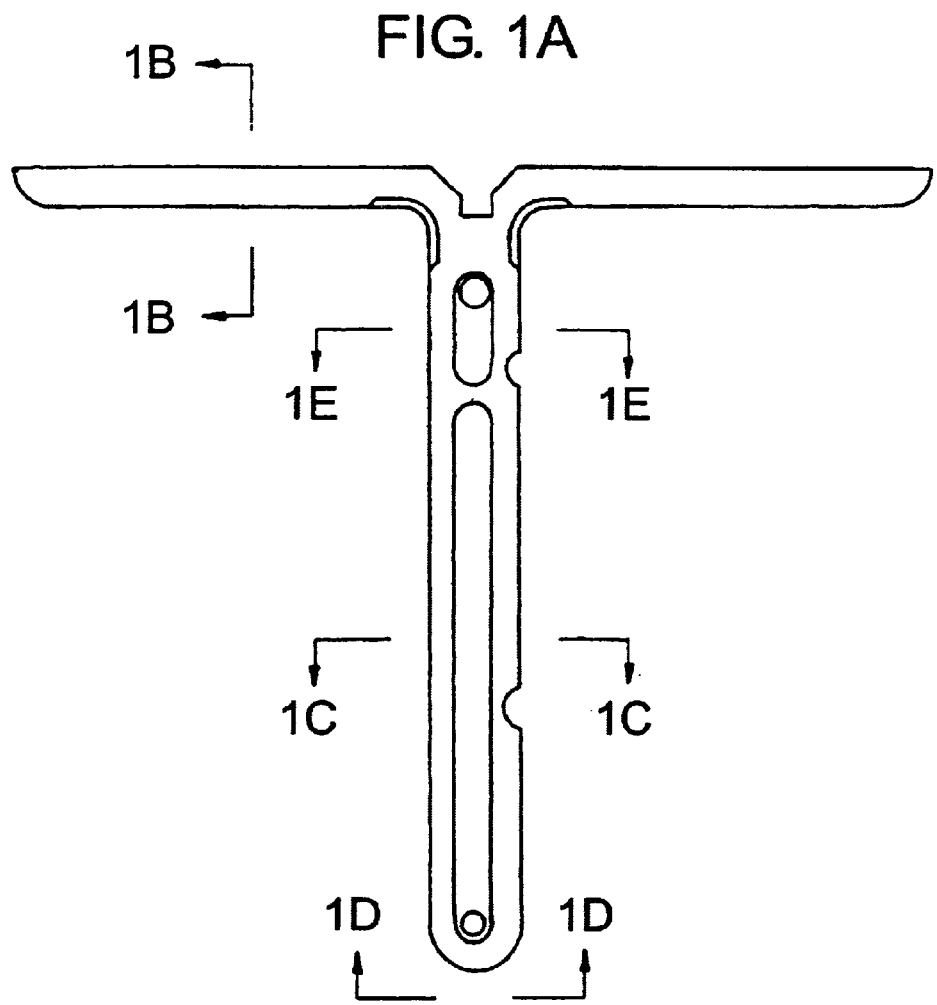
FIG. 1A is an elevation of the "T" shaped device capable of having the top arms thereof resiliently bent to alongside the upstanding body during insertion with an appropriate applicator pull and capable of assuming some return to the "T" form so as to be retained within the vagina of an appropriate animal such as a cattle beast.
Figure 1B:
FIG. 1B is a section at "FF" of the top arms of the "T" form.
Figure 1C:
FIG. 1C is a section at "DD" of the body.
Figure 1E:
FIG. 1E is a section of the body at "EE".
Figure 1D:
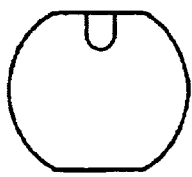
FIG. 1D is a view "CC" of the end of the body showing a slot formed therein from a hole through the body so as to allow the lying therein of a retained withdrawal string or other device.
Figure 2:
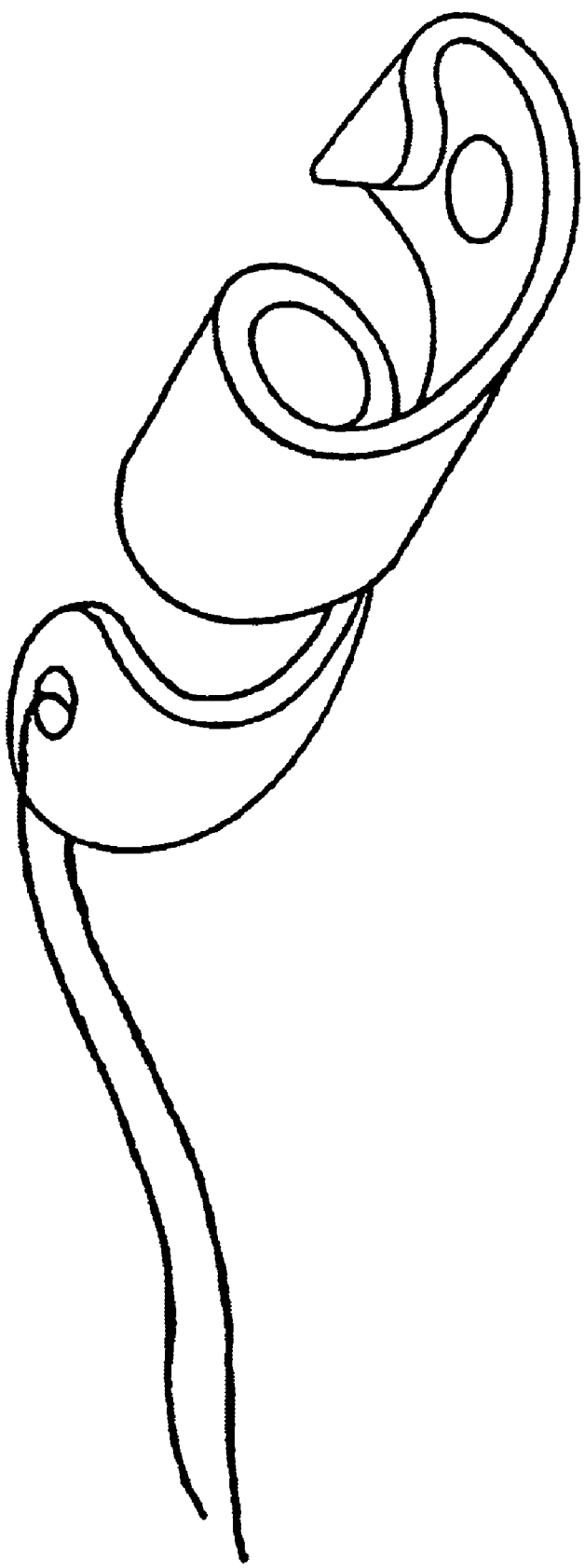
FIG. 2 shows the PRID™ device previously referred to, FIG. 3 shows a preferred device in accordance with the present invention having an average progesterone impregnated matrix of about or less than 1 mm thick over a spine of a kind shown in FIG. 1'.
Figure 4:
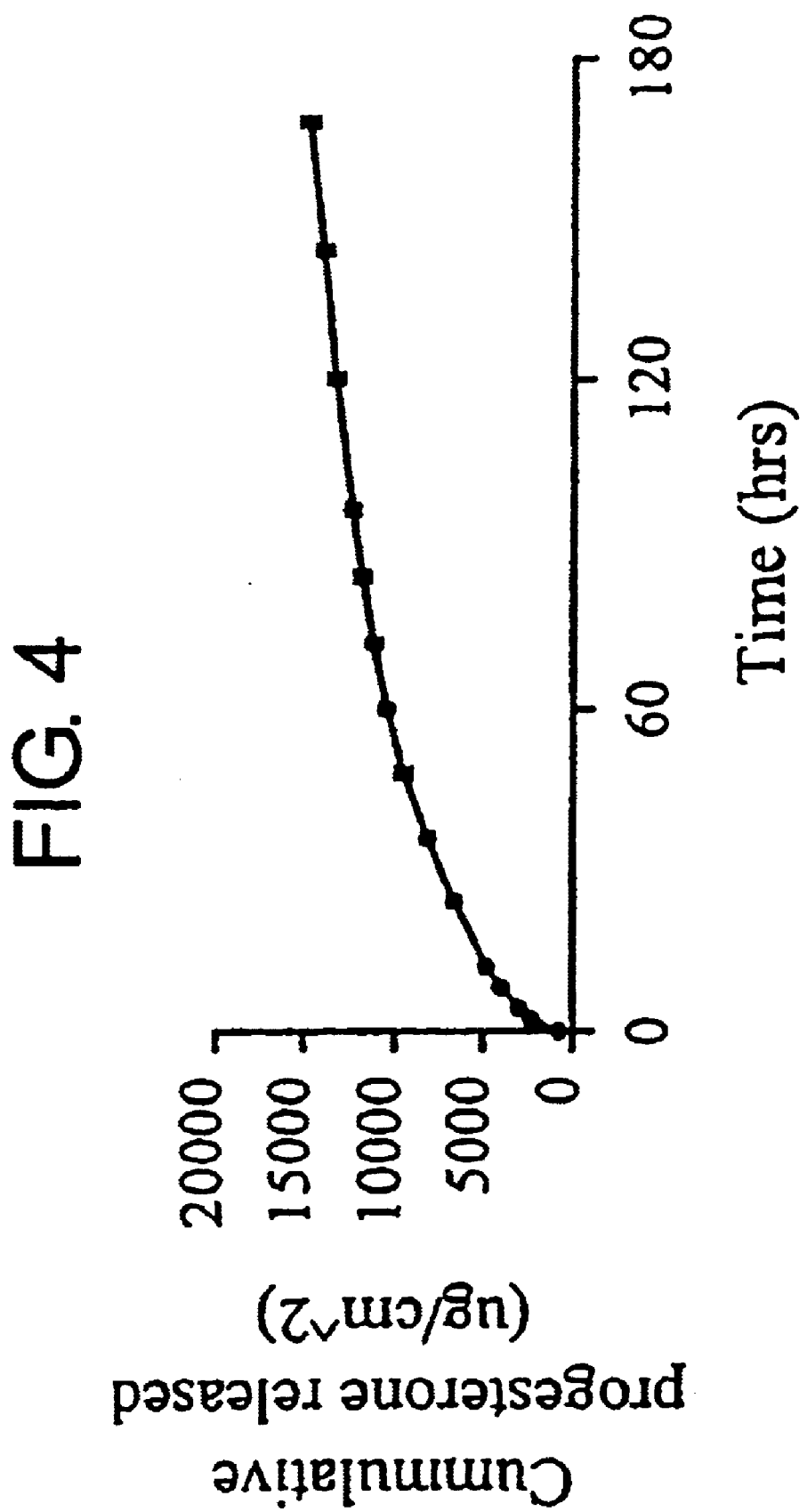

The in vitro release assessment method for the existing CIDR™ device was based on the equipment and general procedures documented in the US Pharmacopoeia, XXIII pp 1791–1975 (1995). In vitro release of progesterone from the device followed a declining profile with time (FIG. 4).

Mechanism of Release

Figure 5:
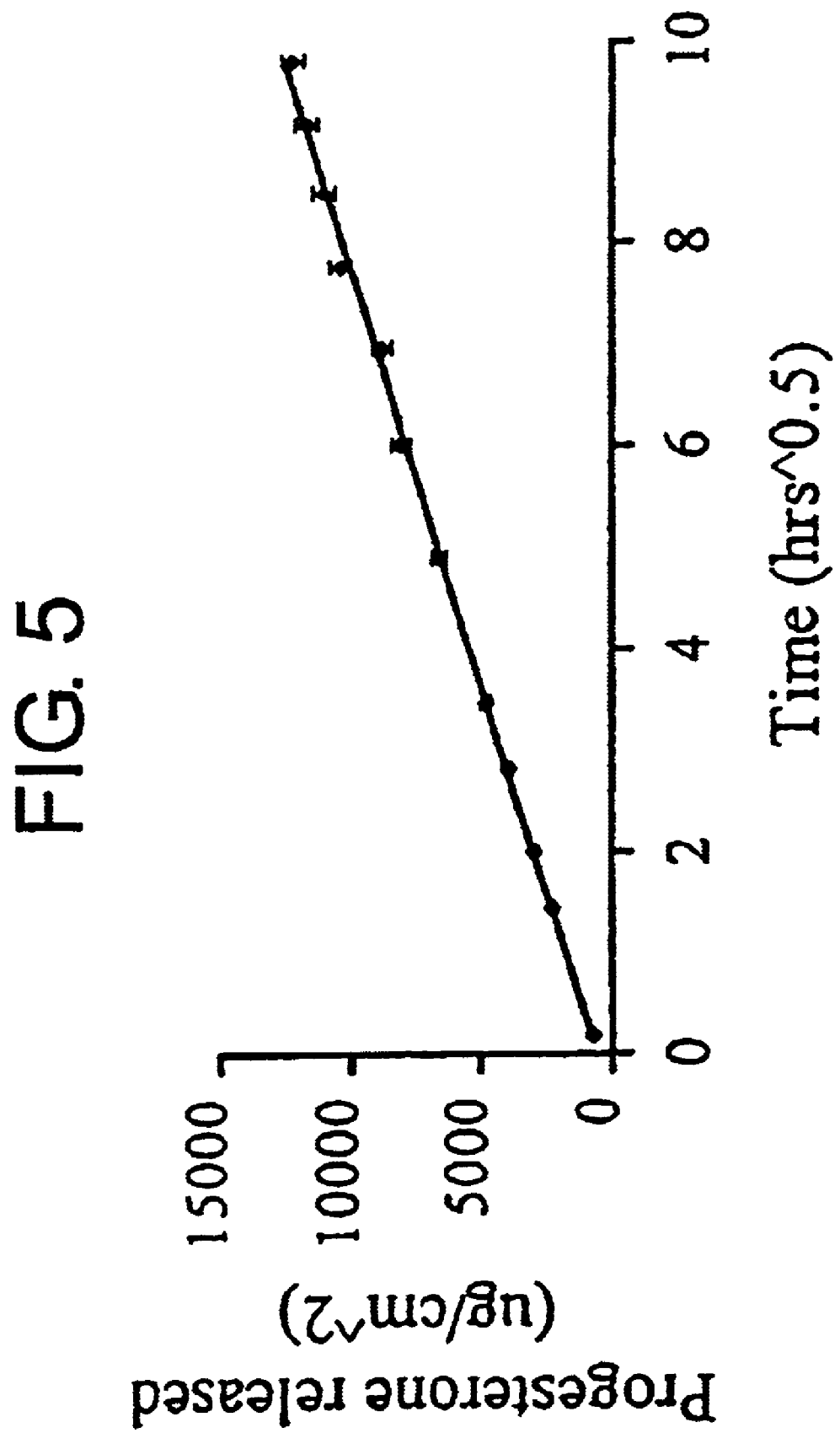

Release data was plotted as cumulative amount of progesterone released per unit area versus square-root-of-time the release profile over greater than 75% of total release from the existing CIDR™ device followed a square-root-of-time model (FIG. 5; linear dependence of progesterone release as a function of the square root of time).

Effect of Drug Load

Figure 6:
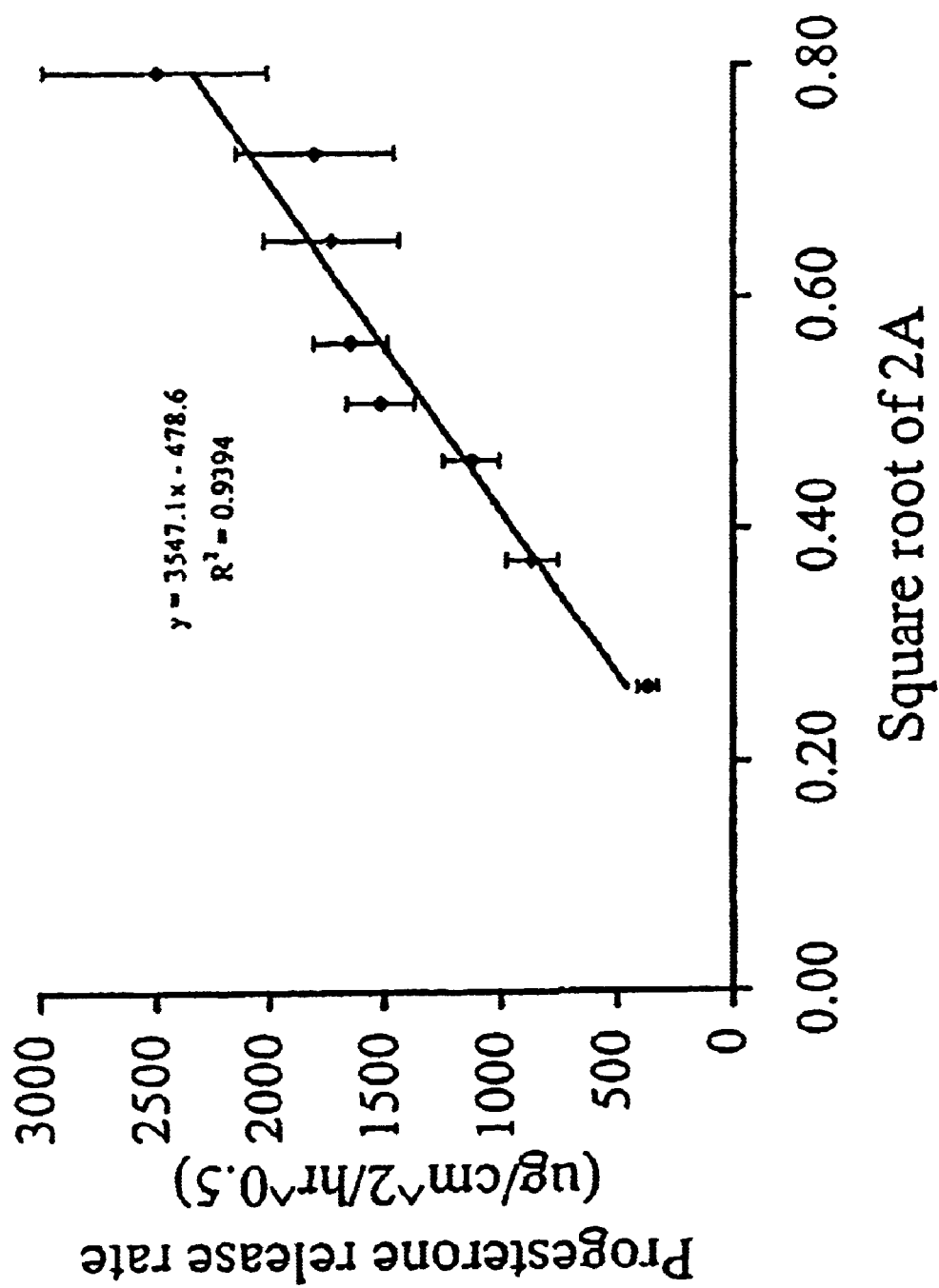

Release rate was observed to be affected by initial drug load as expected from the square-root-of-time model (FIG. 6:—linear dependence of progesterone release rate as a function of the square root of twice the amount of initial drug load).

Determination of the Depletion Zone within Silicone

Figure 7:
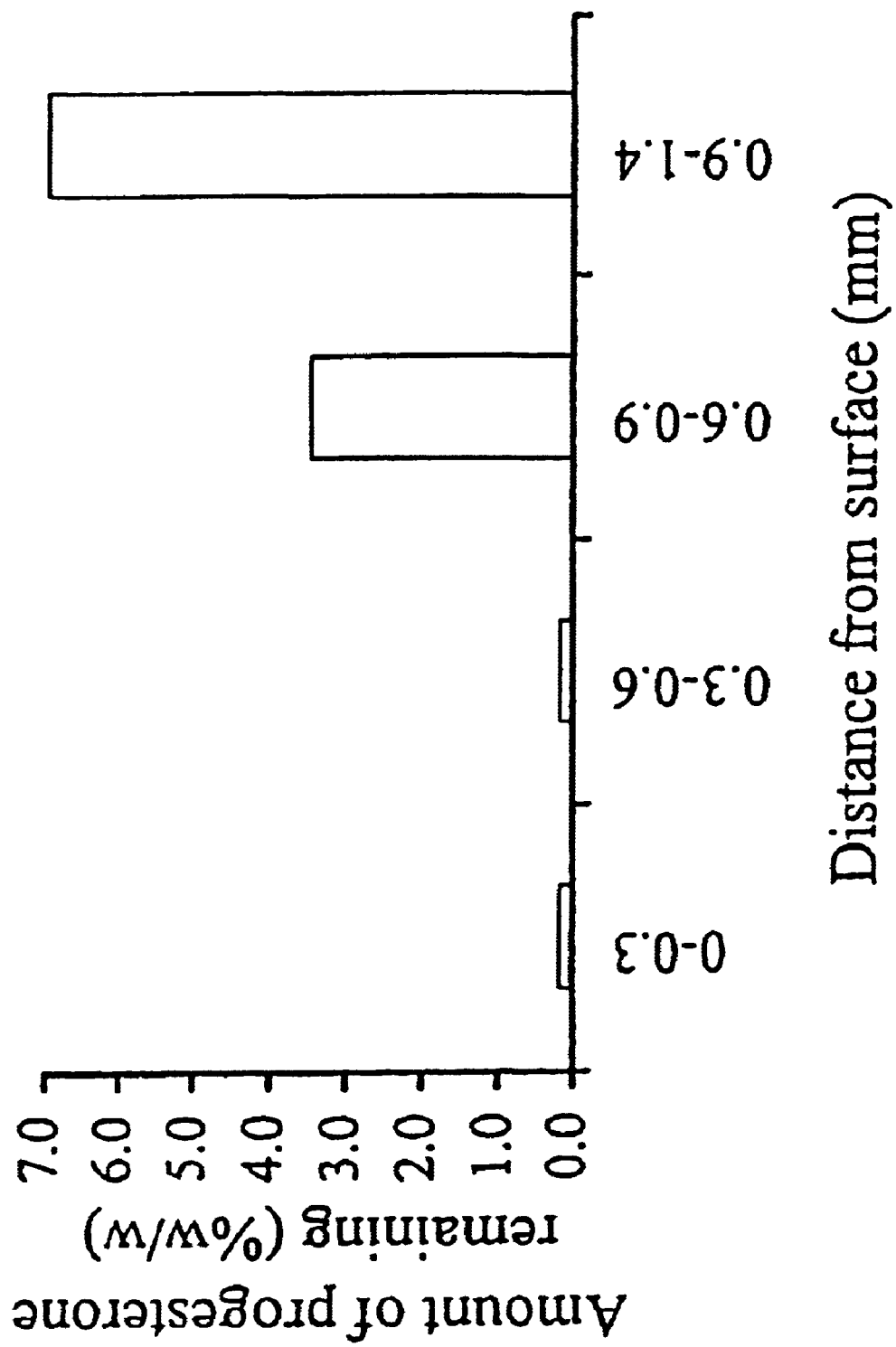
Figure 8:
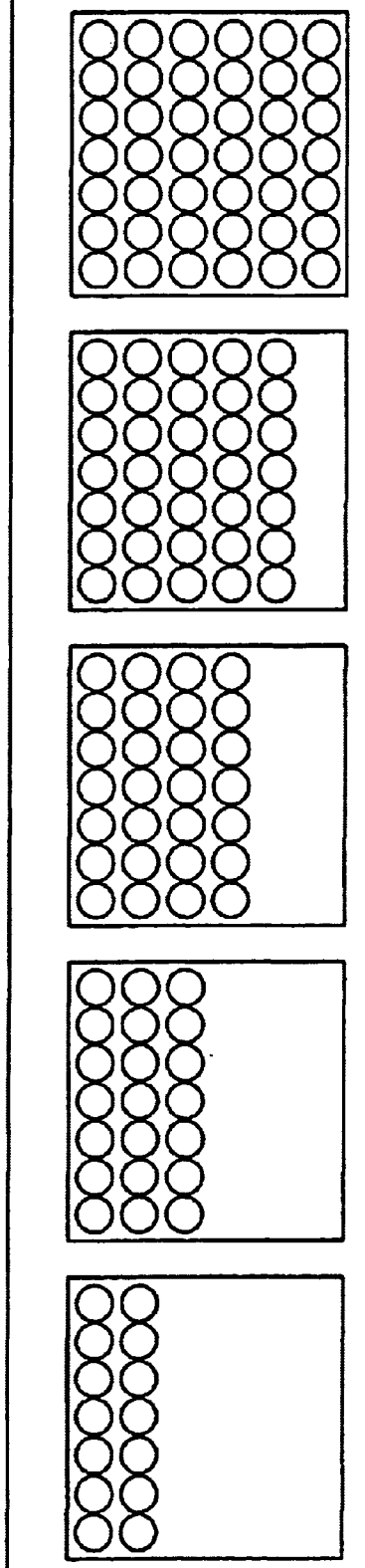

Depletion zone determinations clearly showed the formation of a depletion zone in the silicone skin (FIG. 7) which is consistent with the square-root-of-time theory (FIG. 8).

the results of all in vitro experiments conducted on the CIDR™ device suggested that progesterone was being released from the silicone matrix according to the square-root-of-time model of release.

In vivo Studies

The following in vivo studies which led to our discoveries were conducted on the existing CIDR™ device and on devices of the present invention (i.e., devices referred to as the CIDR-B™ devices).

Blood Level Parameter (Steady-state Blood Level)

Figure 9:
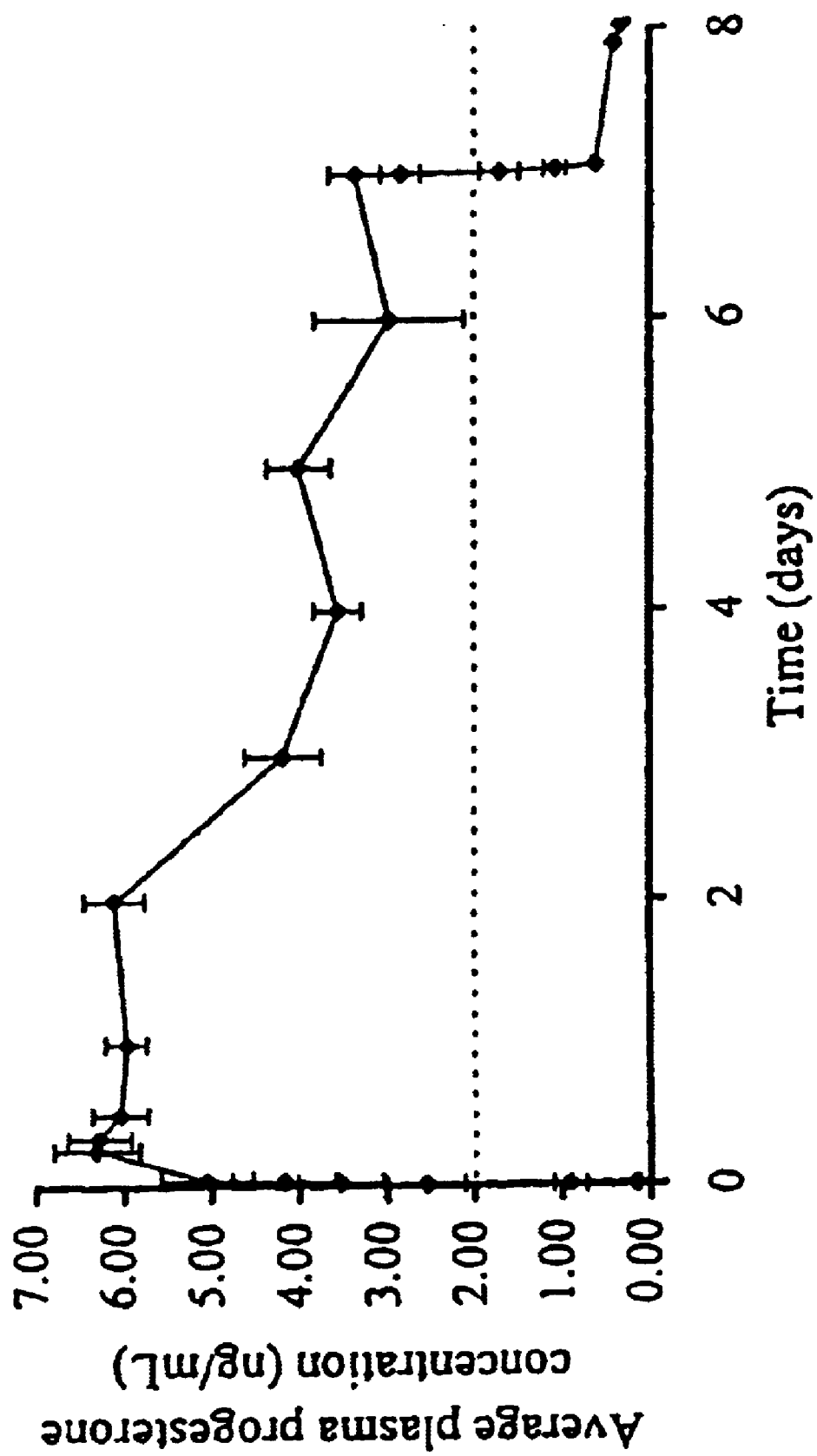

Following insertion of the existing CIDR™ device into ovariectomized cattle a characteristic plasma profile was observed (FIG. 9). There was a rapid absorption phase. Blood levels peaked within a few hours. The peak level was sustained for 48 hours before it fell over the following 24 to 48 hours to levels which were constant or diminished only very slightly over the remaining 4 days of the 7 day insertion period (apparent steady-state levels). Following removal of the device, plasma levels fell rapidly to basal levels. Based on FIG. 9 we selected average progesterone steady-state plasma levels over the last four days of a 7 day insertion period as the performance indicator of the device.

Effect of Initial Progesterone Concentration

Figure 10:
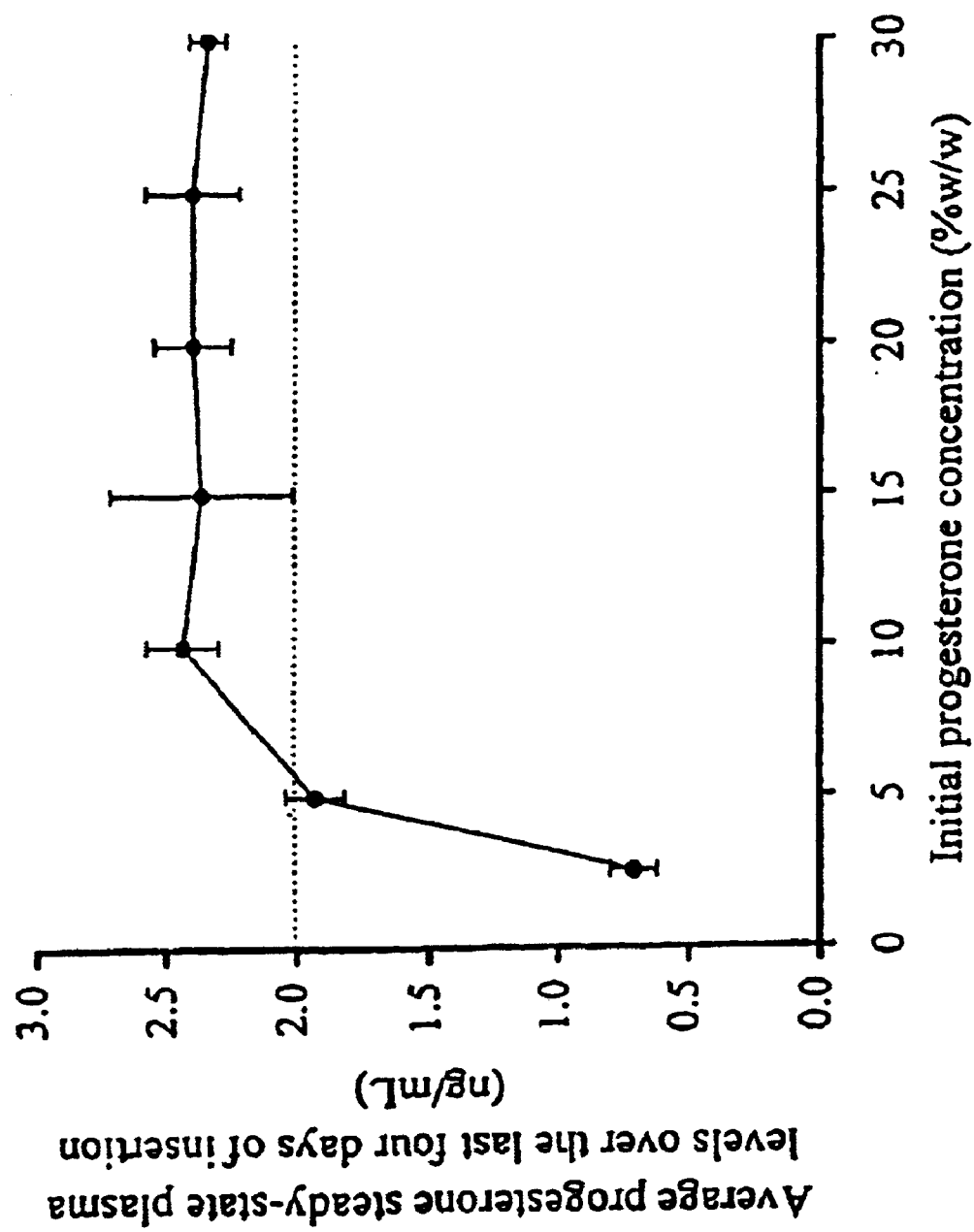

The effect of initial progesterone concentration in the device on the average progesterone steady-state plasma levels over the last four days of a 7 day insertion period is shown in FIG. 10. FIG. 10 shows that the devices containing above a 5% w/w initial progesterone concentration produce average progesterone steady-state plasma levels over the last four days of a 7 day insertion period above 2 ng/mL.

Effect of Surface Area

Figure 11:
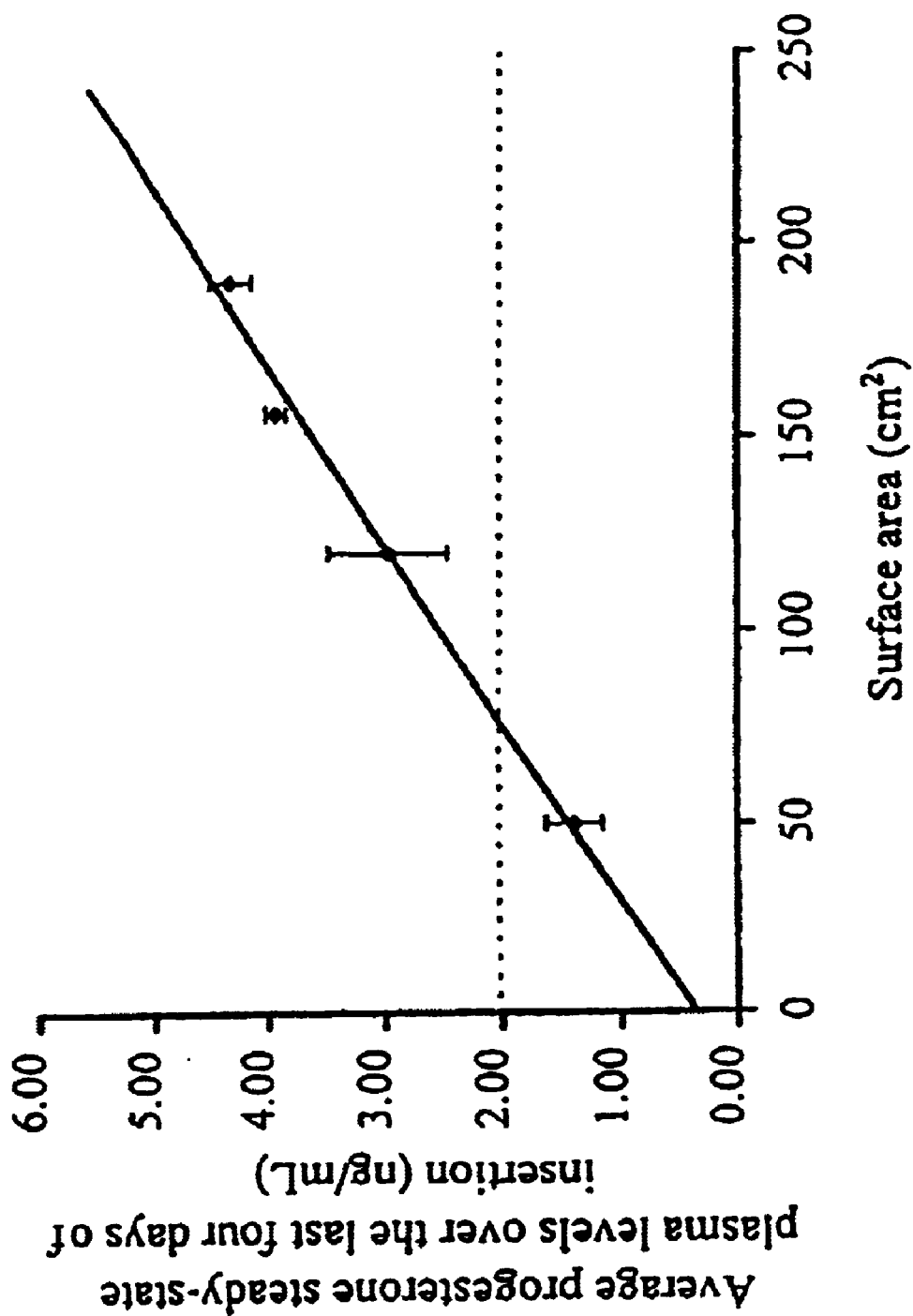

The effect of surface area upon the average progesterone steady-state plasma levels over the last four days of a 7 day insertion period is shown in FIG. 11. An increase in surface area produced an increase in average progesterone steady-state plasma levels over the last four days of a 7 day insertion period (FIG. 11). A surface area of greater than 75 cm$^2$ is required to ensure that average progesterone steady-state plasma levels over the last four days of a 7 day insertion period are above 2 ng/mL.

Determination of the Depletion Zone within Silicone of Used Devices

Figure 12:
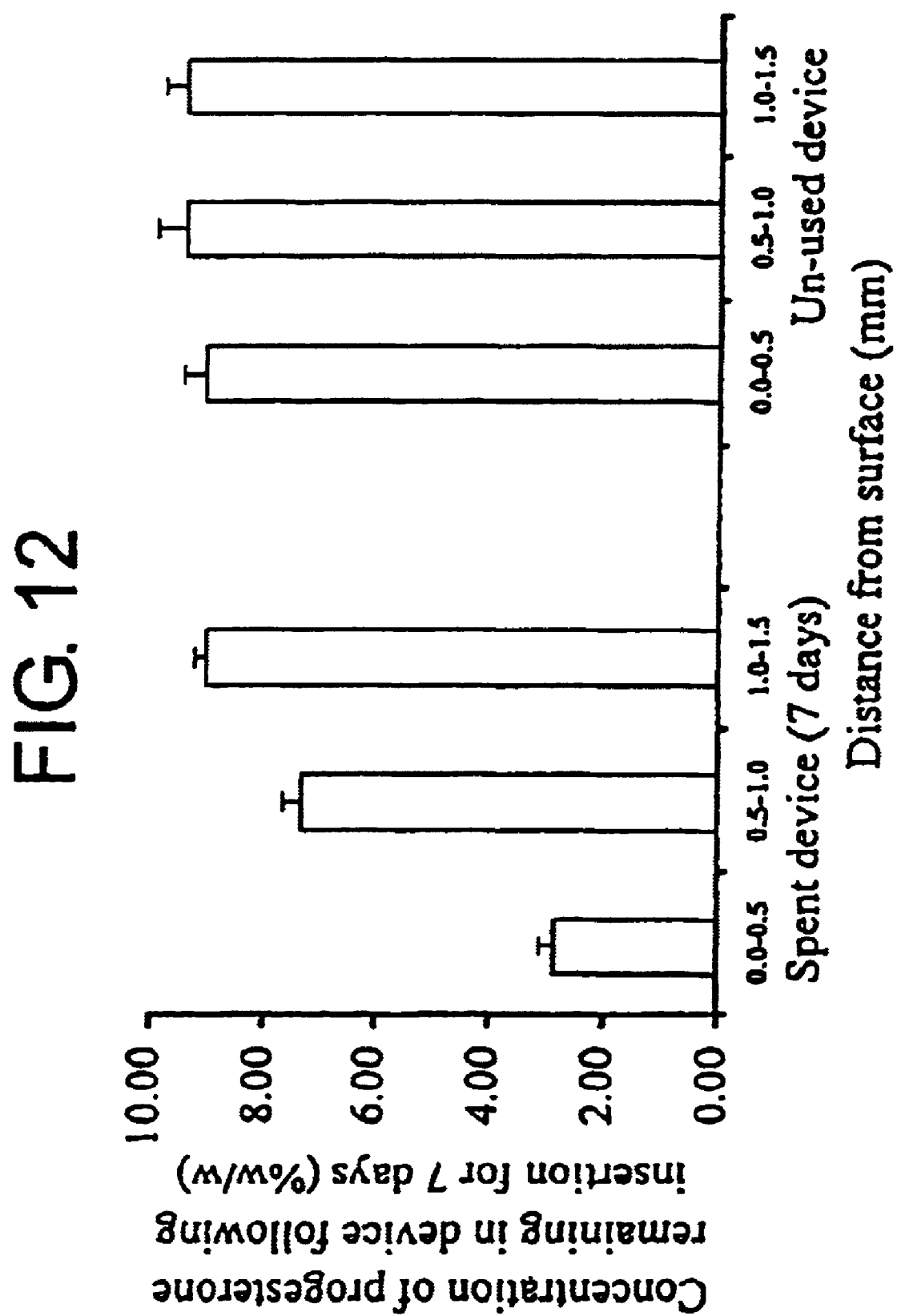
Figure 13:
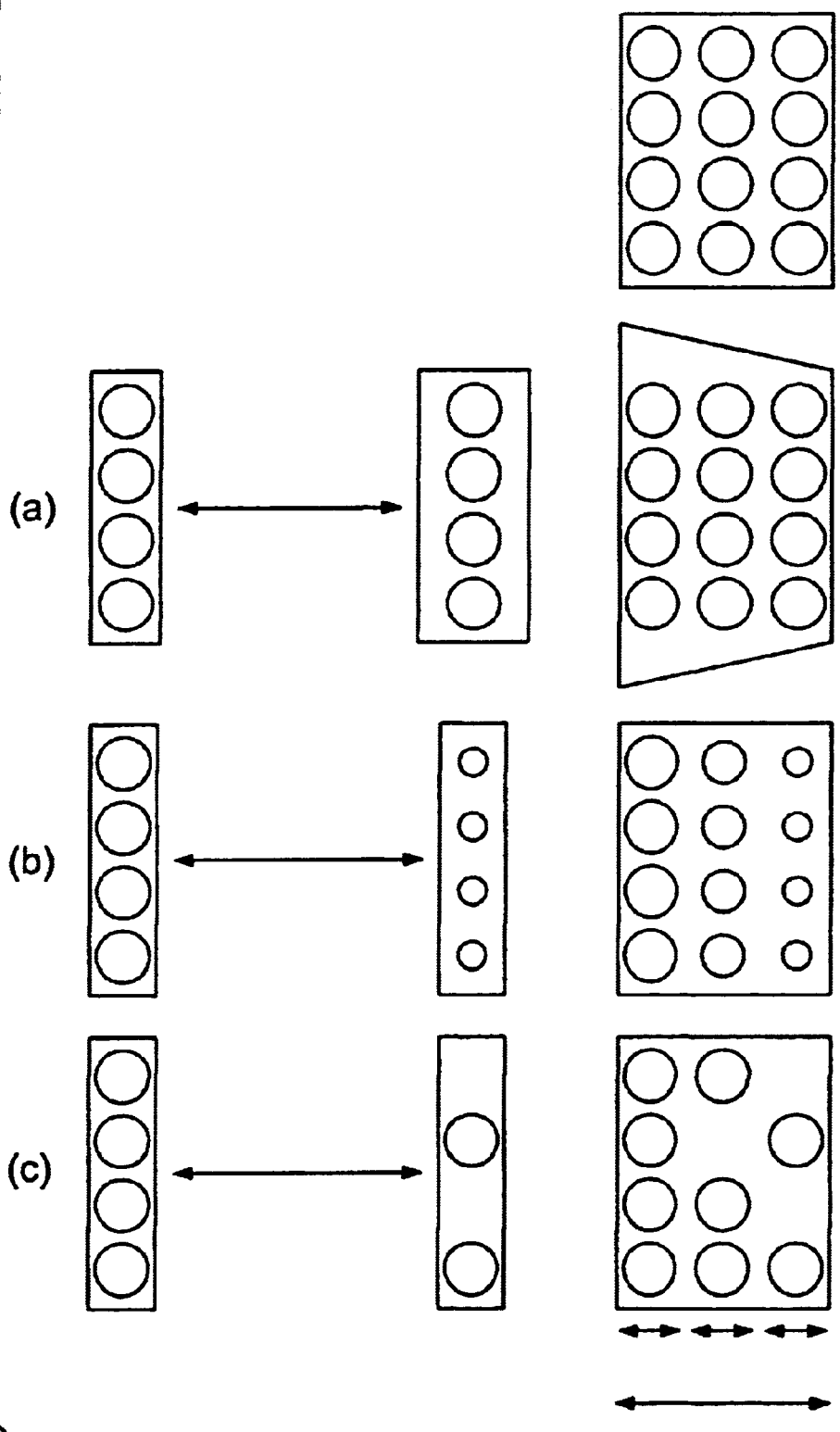
Figure 14:
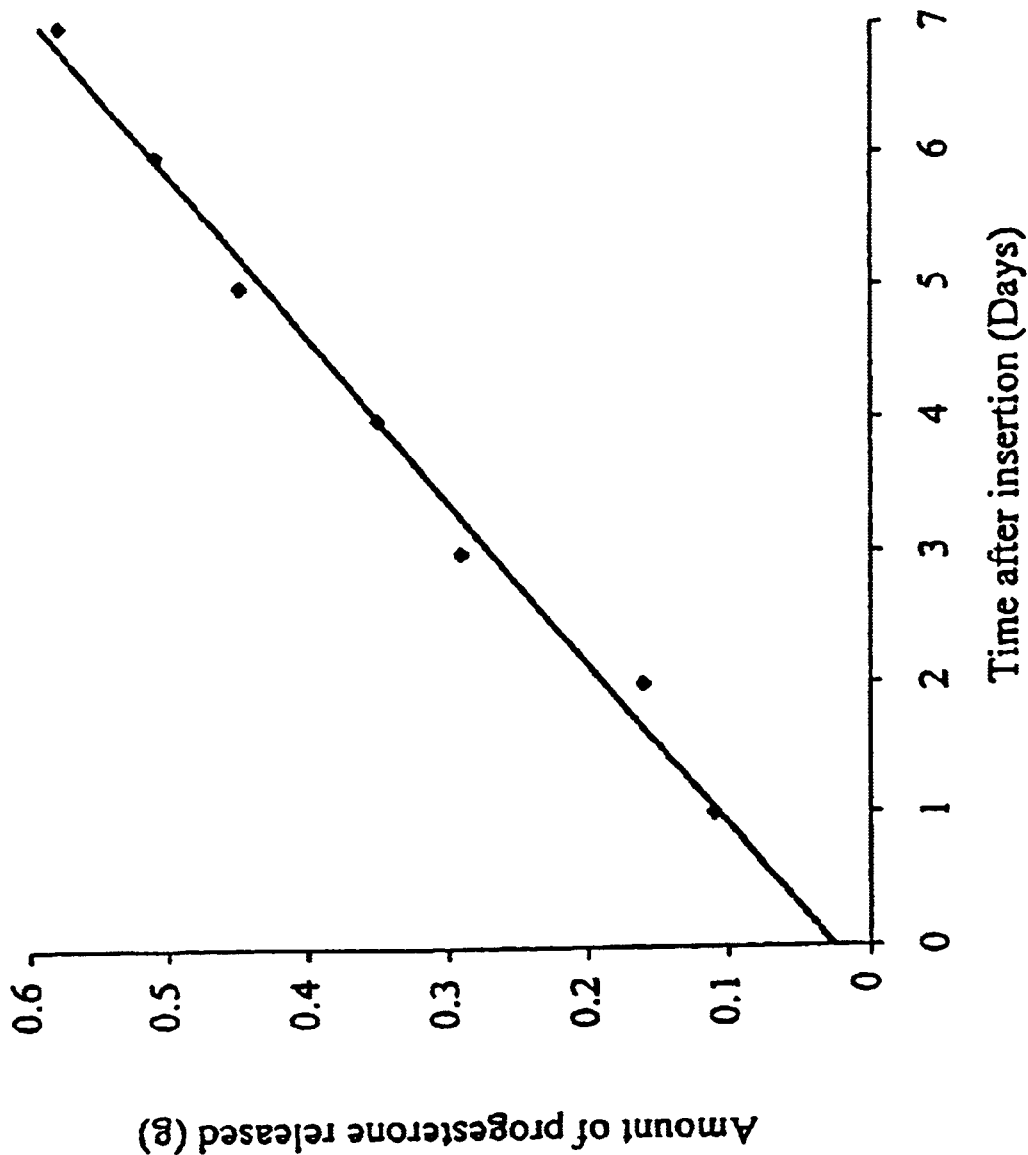

Progesterone concentration at various depths of a spent existing device that had been inserted for 7 days in cattle is shown in FIG. 12. FIG. 12 shows clearly that no distinct depletion zone was apparent following removal of the device after a 7 day insertion period in the vagina of cattle (cf. the clear depletion zone which was observed in the in vitro experiments; FIG. 7). Indeed following in vivo insertion the 0–0.5 mm outermost layer of silicone rubber skin still contained drug but at a concentration less than that originally incorporated into the device, the 0.5–1.0 mm layer also still contained drug but at a concentration less than that originally incorporated into the device. Beyond 1 mm the original amount of progesterone incorporated into the device was detected (FIG. 12). These results (FIG. 12) clearly demonstrate that progesterone was only eluted out of the first 1 mm of silicone rubber skin. The results also suggest that no distinct depletion zone forms as the drug is being released while the device is inside the animal but instead as release occurs a gradation of solid particles forms within the first 1 mm of skin. Possible reasons why such observations were detected are shown in FIG. 13. These observations are not consistent with the square-root-of-time model. Indeed, the in vivo release of progesterone from the device was observed to be constant with time (FIG. 14) and follow a zero-order release mechanism (cf. the declining profile when the amount of progesterone released from the CIDR-B in vitro was plotted against time; FIG. 4).

Investigations on a Device of the Present Invention

From these studies a device was manufactured which had a uniform silicone rubber skin thickness of<1 mm, surface area of 120 cm$^2$ and initially contained 1.25 g (10% w/w) of progesterone. FIG. 15 shows the average progesterone steady-state plasma levels over the last four days of a 7 day insertion period determined for the existing CIDR device and a device in accordance with the present invention (CIDR-B device). FIG. 15 clearly shows that the CIDR-B device is able to effectively sustain progesterone steady-state plasma levels over the last four days of a 7 day insertion period above 2 ng/mL. In addition, the final:initial content ratio for the CIDR-B device is less than 60% following a 7 day insertion period (Table 1).

TABLE 1

Comparison of the initial amount of progesterone, residual progesterone in spent devices and amount of progesterone released from existing CIDR ™ device and device (CIDR-B ™ device) which has characteristics described in this patent application following removal after 7 days.

| Intra vaginal progesterone release device | Initial progesterone concentration in device (% w/w) | Initial amount of progesterone in device (g) | Residual amount of progesterone remaining in device (g) | Amount of progesterone released over 7 days (g) | Final:initial ratio |
|---|---|---|---|---|---|
| Existing CIDR ™ device | 10 | 1.92 | 1.36 | 0.56 | 0.71 |
| Device of the present invention (CIDR-B ™) | 10 | 1.25 | 1.36 | ™ 0.56 | 0.59 |

The following table of in vivo comparative data compares a device in accordance with the present invention (CIDR-B™) with a CIDR™ device and a PRID™ device.

In vivo Comparisons

| Parameter | Existing CIDR ™ device | New CIDR-B ™ device (Present invention) | PRID ™ DEVICE |
|---|---|---|---|
| At least 10% Progesterone in skin | Yes (10%) | Yes (10%) | No (Approx. 7.5%) |
| Progesterone bloods > 2 ng/mL for at least 7 days | Yes | Yes | Yes |
| Initial Progesterone (g) | 1.9 | 1.35 | 1.55 |

| Parameter | Existing CIDR ™ device | New CIDR-B ™ device (Present invention) | PRID ™ DEVICE |
|---|---|---|---|
| Final Progesterone (7 days) | 1.3 | 0.8 | 1.18 |
| Final Progesterone (10 days) | 1.18 | 0.63 | 0.94 |
| Final/Initial (7 days) | 0.68 | 0.59 | 0.76 |
| Final/Initial (10 days) | 0.62 | 0.47 | 0.61 |
| Skin thickness (mm) | Variable (0.9–5) | 1.0 | 1.0 |
| Surface area (cm$^2$) | 120 | 120 | 220 |

The device of the present invention (CIDR-B ™)

The device (CIDR-B™) consists of a progesterone impregnated silicone elastomer skin moulded over an inert nylon spine. The active ingredient of the device is micronised USP natural progesterone. Device potency is determined by the percentage of active ingredient present in the inactive silicone elastomer.

The progesterone is mixed into each of two liquid silicone parts prior to the silicone being introduced to the machine for moulding. The progesterone is preferably mixed in at 10% by total weight.

At the moulding stage the two parts of the liquid silicone are pumped under pressure of approximately 100 bar from pails into the injection chambers of an injection moulding machine. Upon injection, the two parts of silicone are simultaneously forced through a static mixer before flowing into an electrically heated mould.

The nylon spine is inserted into the mould prior to the silicone being injected. The mould has a die surface temperature of typically 190°–195° C., but preferably never exceeding 200° C. The mould is kept clamped shut under approximately 30 tonnes of static pressure while the silicone cures. At the indicated temperature and pressure, the liquid silicone takes approximately 50 seconds to cure into a rubber.

Following curing, the finished product is removed from the mould and cooled before packaging.

The surface area of the silicone skin is approximately 120–125 cm$^2$ with the typical formulation for the device being:

| Outer Skin (impregnated Matrix) | Nominal Weight (gm) | Percentage of Skin | Percentage of Device |
|---|---|---|---|
| Active progesterone USP | 1.35 | 10% | 5.1% |
| Inactive silicone elastomer | 12.15 | 90% | 45.9% |

What we claim is:

1. A method of postponing oestrus or treating anoestrus in an animal, said method comprising the steps of moulding a progesterone impregnated silicone rubber matrix having a progesterone content in the matrix of 5% or greater by weight, a total progesterone load of at least one gram, a surface area greater than 75 cm$^2$, and at least substantially all of the progesterone in the matrix being less than one millimeter away from a release surface, administering the progesterone impregnated silicone rubber matrix intra vaginally in the animal, maintaining the matrix in position until achieving an ultimate progesterone blood plasma level in the animal of from 2 to about 4 nanograms per milliliter, and removing the device after an insertion period of from 5 to 12 days with a residual load of progesterone in the matrix being less than 65% by weight of an initial progesterone load during the administering step.

2. The method of claim 1, wherein oestradiol is at or near the time of insertion of said device.

3. The method of claim 1, wherein a prostaglandin is administered into the animal at about day 6 of one of about a 7 day and about a 10 day device insertion period.

4. A method of synchronizing the onset of oestrus in a herd of cattle beasts, said method comprising moulding a progesterone impregnated silicone rubber matrix having a progesterone content in the matrix of 5% or greater by weight, a total progesterone load of at least one gram, a surface area greater than 75 cm$^2$, and at least substantially all of the progesterone in the matrix being less than one millimeter away from a release surface, and administering to each animal from the progesterone impregnated silicone matrix an effective amount of progesterone over a time period of from 5 to 12 days while the matrix is retained intra vaginally such that the matrix is administered with an initial progesterone quantity of about 1.35 grams and is removed with a progesterone quantity of about 0.85 grams thereby producing an ultimate progesterone blood plasma level in the animal of from 2 to about 4 nanograms per milliter.

5. An intra vaginal device capable of being applied into the vaginal cavity of a targeted species animal selected from the group consisting of cattle, sheep, deer and goats, retainable therein over a period of time and then to be withdrawable therefrom to allow the onset of oestrus, said device having a resilient frame that provides two arms capable of being moved towards each other against the resilience thereof so as, in its vaginal cavity retainable form, to provide an outward pressure reliant upon the vaginal cavity contained splayed condition of the arms thereof, and one or more masses carried by the frame to provide a matrix of a progesterone impregnated silicon rubber, said matrix having greater than 5% by weight progesterone to the weight of the matrix, defining at least one progesterone release surface in total of at least 75 cm$^2$ contactable once inserted in the vagina of such an animal by the vaginal membrane and/or vaginal fluid(s) of the animal, having a total progesterone load, irrespective of whether alpha or beta progesterone or mixtures thereof, of at least 1 gram, and having at least substantially all of the progesterone in the matrix less than 1 millimeter away from said release surface;

and wherein said device upon vaginal insertion into such an animal for which it is sized and targeted, is able to achieve and then maintain in the animal for at least seven days a minimum progesterone blood plasma level of 2 nanograms per millimeter of plasma of the animal, and should the device have been vaginally inserted in such an animal for which it is sized and targeted for seven days, will have a residual load of progesterone in the matrix of less than 65% by weight of its progesterone load at insert.

6. The device as claimed in claim 5 wherein the mass or each mass of the progesterone containing matrix has been formed by injection of uncured progesterone containing matrix as a liquid into a mould for a sufficient time to achieve at an elevated mould temperature a shape retaining at least partial cure thereof.

7. The device as claimed in claim 5 wherein the release surface of the mass or masses of the matrix provide a total progesterone release surface of from 100 to 1500 $cm^2$.

* * * * *